United States Patent
Heaton et al.

(10) Patent No.: US 8,114,126 B2
(45) Date of Patent: Feb. 14, 2012

(54) MODULAR, REDUCED-PRESSURE, WOUND-CLOSURE SYSTEMS AND METHODS

(75) Inventors: Keith Patrick Heaton, Poole (GB); Ian James Hardman, Bournemouth (GB); Christopher Guy Coward, Wareham (GB); Colin John Hall, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 354 days.

(21) Appl. No.: 12/467,199

(22) Filed: May 15, 2009

(65) Prior Publication Data

US 2010/0106188 A1    Apr. 29, 2010

Related U.S. Application Data

(60) Provisional application No. 61/109,410, filed on Oct. 29, 2008, provisional application No. 61/109,486, filed on Oct. 29, 2008, provisional application No. 61/109,390, filed on Oct. 29, 2008, provisional application No. 61/109,448, filed on Oct. 29, 2008.

(51) Int. Cl.
*A61B 17/08*  (2006.01)
*A61D 1/00*   (2006.01)
*A61F 13/00*  (2006.01)
*A61F 15/00*  (2006.01)
*A61M 5/32*   (2006.01)

(52) U.S. Cl. ............................ 606/216; 602/42; 604/176
(58) Field of Classification Search .......... 604/174–180, 604/290, 307, 308, 313, 315, 317, 319, 327, 604/378, 385.01, 543; 602/41–43, 46, 59, 602/57, 47, 53; 606/151, 201, 213, 215, 606/216, 131; 623/23.72, 23.76; 600/201, 600/208, 215, 216
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |

(Continued)

FOREIGN PATENT DOCUMENTS

AU    550575 A1    8/1982

(Continued)

OTHER PUBLICATIONS

Restriction Requirement dated Jan. 4, 2010 in U.S. Appl. No. 12/466,973.

(Continued)

*Primary Examiner* — Kathleen Sonnett
*Assistant Examiner* — Jocelin Tanner
(74) *Attorney, Agent, or Firm* — SNR Denton US LLP (57) ABSTRACT

A modular, reduced-pressure, wound-closure system for generating a closing force on a surface wound on a patient includes a sealed contracting member, a plurality of attachment base members, and a plurality of connecting members. The combination of the plurality of attachment base members and plurality of connecting members forms a circumferential wall around the surface wound. The sealed contracting member is operable to be disposed within an interior space defined by the circumferential wall and coupled to at least of portion of the circumferential wall. When reduced pressure is provided to the sealed contracting member, the sealed contracting member contracts and the circumferential wall delivers a closing force. Other systems and methods are presented.

22 Claims, 4 Drawing Sheets

U.S. PATENT DOCUMENTS

| | | | |
|---|---|---|---|
| 3,367,332 | A | 2/1968 | Groves |
| 3,520,300 | A | 7/1970 | Flower, Jr. |
| 3,556,101 | A | 1/1971 | Economou |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 3,830,238 | A | 8/1974 | Kurtz et al. |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,250,882 | A | 2/1981 | Adair |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,294,240 | A | 10/1981 | Thill |
| 4,297,995 | A | 11/1981 | Golub |
| 4,333,468 | A | 6/1982 | Geist |
| 4,346,711 | A | 8/1982 | Agdanowski et al. |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,430,084 | A | 2/1984 | Deaton |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,633,865 | A | 1/1987 | Hengstberger et al. |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,728,642 | A | 3/1988 | Pawelchak et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,815,468 | A | 3/1989 | Annand |
| 4,825,866 | A | 5/1989 | Pierce |
| 4,826,494 | A | 5/1989 | Richmond et al. |
| 4,838,883 | A | 6/1989 | Matsuura |
| 4,840,187 | A | 6/1989 | Brazier |
| 4,844,072 | A | 7/1989 | French et al. |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,899,965 | A | 2/1990 | Usui |
| 4,906,233 | A | 3/1990 | Moriuchi et al. |
| 4,906,240 | A | 3/1990 | Reed et al. |
| 4,908,350 | A | 3/1990 | Kramer et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,192,266 | A | 3/1993 | Wilk |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,437,683 | A | 8/1995 | Neumann et al. |
| 5,441,481 | A | 8/1995 | Mishra et al. |
| 5,443,848 | A | 8/1995 | Kramer et al. |
| 5,466,231 | A | 11/1995 | Cercone et al. |
| 5,484,399 | A | 1/1996 | DiResta et al. |
| 5,484,428 | A | 1/1996 | Drainvill et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,637,103 | A | 6/1997 | Kerwin et al. |
| 5,645,081 | A | 7/1997 | Argenta et al. |
| 5,662,598 | A | 9/1997 | Tobin |
| 5,701,917 | A | 12/1997 | Khouri |
| 5,792,173 | A | 8/1998 | Breen et al. |
| 5,893,368 | A | 4/1999 | Sugerman |
| 5,902,260 | A | 5/1999 | Gilman et al. |
| 5,938,626 | A | 8/1999 | Sugerman |
| 6,042,539 | A | 3/2000 | Harper et al. |
| 6,051,747 | A | 4/2000 | Lindqvist et al. |
| 6,071,267 | A | 6/2000 | Zamierowski |
| 6,135,116 | A | 10/2000 | Vogel et al. |
| 6,174,306 | B1 | 1/2001 | Fleischmann |
| 6,241,747 | B1 | 6/2001 | Ruff |
| 6,264,979 | B1 | 7/2001 | Svedman |
| 6,287,316 | B1 | 9/2001 | Agarwal et al. |
| 6,345,623 | B1 | 2/2002 | Heaton et al. |
| 6,383,162 | B1 | 5/2002 | Sugarbaker |
| 6,458,109 | B1 | 10/2002 | Henley et al. |
| 6,488,643 | B1 | 12/2002 | Tumey et al. |
| 6,493,568 | B1 | 12/2002 | Bell et al. |
| 6,537,241 | B1 | 3/2003 | Odland |
| 6,553,998 | B2 | 4/2003 | Heaton et al. |
| 6,626,891 | B2 | 9/2003 | Ohmstede |
| 6,685,681 | B2 | 2/2004 | Lockwood et al. |
| 6,695,823 | B1 | 2/2004 | Line et al. |
| 6,752,794 | B2 | 6/2004 | Lockwood et al. |
| 6,814,079 | B2 | 11/2004 | Heaton et al. |
| 6,855,135 | B2 | 2/2005 | Lockwood et al. |
| 6,936,037 | B2 | 8/2005 | Bubb et al. |
| 6,951,553 | B2 | 10/2005 | Bubb et al. |
| 6,979,324 | B2 | 12/2005 | Bybordi et al. |
| 7,105,001 | B2 | 9/2006 | Mandelbaum |
| 7,128,735 | B2 | 10/2006 | Weston |
| 7,195,624 | B2 | 3/2007 | Lockwood et al. |
| 7,276,051 | B1 | 10/2007 | Henley et al. |
| 7,338,482 | B2 | 3/2008 | Lockwood et al. |
| 7,381,859 | B2 | 6/2008 | Hunt et al. |
| 7,476,205 | B2 | 1/2009 | Erdmann |
| 7,951,100 | B2 | 5/2011 | Hunt et al. |
| 2002/0062097 | A1 | 5/2002 | Simpson |
| 2002/0065494 | A1 | 5/2002 | Lockwood et al. |
| 2002/0077661 | A1 | 6/2002 | Saadat |
| 2002/0115951 | A1 | 8/2002 | Norstrem et al. |
| 2002/0115956 | A1 | 8/2002 | Ross |
| 2002/0120185 | A1 | 8/2002 | Johnson |
| 2002/0143286 | A1 | 10/2002 | Tumey |
| 2002/0161317 | A1 | 10/2002 | Risk et al. |
| 2003/0208149 | A1 | 11/2003 | Coffey |
| 2005/0085795 | A1 | 4/2005 | Lockwood |
| 2005/0101922 | A1 | 5/2005 | Anderson et al. |
| 2005/0131327 | A1 | 6/2005 | Lockwood et al. |
| 2005/0261642 | A1 | 11/2005 | Weston |
| 2005/0273066 | A1 | 12/2005 | Wittmann |
| 2006/0029650 | A1 | 2/2006 | Coffey |

| | | | |
|---|---|---|---|
| 2006/0041247 | A1 | 2/2006 | Petrosenko et al. |
| 2006/0079852 | A1 | 4/2006 | Bubb |
| 2006/0189910 | A1 | 8/2006 | Johnson et al. |
| 2007/0282309 | A1 | 12/2007 | Bengtson et al. |
| 2008/0058684 | A1 | 3/2008 | Ugander et al. |
| 2008/0167593 | A1 | 7/2008 | Fleischmann |
| 2009/0099519 | A1 | 4/2009 | Kaplan |
| 2010/0030132 | A1 | 2/2010 | Niezgoda et al. |

FOREIGN PATENT DOCUMENTS

| | | |
|---|---|---|
| AU | 745271 | 4/1999 |
| AU | 755496 | 2/2002 |
| CA | 2005436 | 6/1990 |
| CA | 2 303 085 | 3/1999 |
| DE | 26 40 413 A1 | 3/1978 |
| DE | 2754775 A1 | 6/1979 |
| DE | 43 06 478 A1 | 9/1994 |
| DE | 295 04 378 U1 | 10/1995 |
| DE | 20115990 U1 | 12/2001 |
| DE | 69806842 T2 | 1/2003 |
| DE | 60118546 T2 | 8/2006 |
| DE | 102006032870 | 1/2008 |
| EP | 0100148 A1 | 2/1984 |
| EP | 0117632 A2 | 9/1984 |
| EP | 0161865 A2 | 11/1985 |
| EP | 271491 B1 | 6/1988 |
| EP | 0358302 A2 | 3/1990 |
| EP | 0506992 | 10/1992 |
| EP | 0555293 | 8/1993 |
| EP | 0777504 | 6/1997 |
| EP | 0 853 950 B1 | 10/2002 |
| EP | 1284777 | 2/2003 |
| EP | 1 088 569 B1 | 8/2003 |
| EP | 1018967 B1 | 8/2004 |
| EP | 0 688 189 B2 | 6/2005 |
| EP | 0 620 720 B2 | 11/2006 |
| GB | 692578 | 6/1953 |
| GB | 2058227 A | 4/1981 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2342584 A | 4/2000 |
| GB | 2 329 127 B | 8/2000 |
| GB | 2365350 | 2/2002 |
| JP | 3056429 U | 5/1991 |
| JP | 4129536 | 4/1992 |
| SG | 71559 | 4/2002 |
| WO | WO 80/02182 | 10/1980 |
| WO | WO 87/01027 A1 | 2/1987 |
| WO | WO 87/04626 | 8/1987 |
| WO | WO 90/10424 | 9/1990 |
| WO | WO 92/07519 A1 | 5/1992 |
| WO | WO 93/09727 | 5/1993 |
| WO | WO 94/20041 | 9/1994 |
| WO | WO 96/05873 | 2/1996 |
| WO | WO 96/34636 A | 11/1996 |
| WO | WO 97/18007 | 5/1997 |
| WO | WO 99/01173 A1 | 1/1999 |
| WO | WO 99/13793 | 3/1999 |
| WO | WO 00/07653 A1 | 2/2000 |
| WO | WO 00/42958 A1 | 7/2000 |
| WO | WO 00/57794 A1 | 10/2000 |
| WO | WO 00/59418 A1 | 10/2000 |
| WO | WO 00/59424 A1 | 10/2000 |
| WO | WO 01/34223 A1 | 5/2001 |
| WO | WO 01/71231 A1 | 9/2001 |
| WO | WO 01/85248 A | 11/2001 |
| WO | WO 01/89431 A1 | 11/2001 |
| WO | WO 03/057307 A1 | 7/2003 |
| WO | WO 03/086232 | 10/2003 |
| WO | WO 2006/048246 A1 | 5/2006 |
| WO | WO 2006/114637 A2 | 11/2006 |
| WO | WO 2007/031762 A | 3/2007 |
| WO | WO 2007/041642 A | 4/2007 |
| WO | WO 2007/109209 A2 | 9/2007 |
| WO | WO 2007/133618 A2 | 11/2007 |
| WO | WO 2008/014358 A2 | 1/2008 |
| WO | WO 2008/040020 A | 4/2008 |
| WO | WO 2008/041926 A1 | 4/2008 |
| WO | WO 2008/103625 A2 | 8/2008 |

OTHER PUBLICATIONS

Response filed Jan. 21, 2010 to Restriction Requirement dated Jan. 4, 2010 in U.S. Appl. No. 12/466,973.

Non-Final Action date mailed Mar. 5, 2010 in U.S. Appl. No. 12/466,973.

Kubiak et al, "Peritoneal Negative Pressure Therapy Prevents Multiple Organ Injury in a Chronic Porcine Sepsis and Ischemia/Reperfusion Model", SHOCK, vol. 34, No. 5, pp. 525-534, 2010.

Response filed Nov. 9, 2010 for U.S. Appl. No. 12/127,668.

Notice of Allowance date mailed Dec. 6, 2010 for U.S. Appl. No. 12/127,668.

Response filed May 20, 2010 to Non-Final Action date mailed Mar. 5, 2010 in U.S. Appl. No. 12/466,973.

N. A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (copy and certified translation).

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, Managing Draining Wounds and Fistulae: "New and Established Methods," *Chronic Wound Care*, edited by D. Krasner (Health Management Publications, Inc., King of Prussia, PA 1990), pp. 240-246.

G. Živadinović, V. Ðukić, Ž., Maksimović, Ð. Radak, and P. Peška, "Vacuum Therapy in the Treatment of Peripheral Blood Vessels," *Timok Medical Journal* 11 (1986), pp. 161-164 (copy and certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax, " *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N. A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

The V.A.C. TM Vacuum Assisted Closure, Assisting in Wound Closure, Brochure, Jan. 1996, 5 pages, 1-A-042, KCI®, San Antonio, Texas.

Argenta et al: "The V.A.C. TM, Case Study #4", Case Study, Mar. 1995, 1 page, 35-D-004, KCI®, San Antonio, Texas.

Argenta et al: "The V.A.C. TM, Case Study #3", Case Study, Mar. 1995, 1 page, 35-D-003, KCI®, San Antonio, Texas.

"The V.A.C. ® Operations Summary, The V.A.C. ® Wound Closure System Appications", Brochure, Mar. 1997, 4 pages, 1-A-060, KCI ®, San Antonio, Texas.

"The V.A.C. ® Operations Summary, The V.A.C. ® Wound Closure System Applcations", Brochure, Mar. 1999, 2 pages, 1-A-060, KCI ®, San Antonio, Texas.

Argenta et al.: "V.AC. ® Wound Closure Device Case Study #3", Case Study, Apr. 1998, 1 page, 35-D-003, KCI®, San Antonio, Texas.

Argenta et al.: "V.AC. ® Wound Closure Device Case Study #1", Case Study, Apr. 1998, 1 page, 35-D-001, KCI®, San Antonio, Texas.

The V.A.C.® Case Study #8, Case Study, Jun. 1996, 2 pages, 35-D-008, KCI®, San Antonio, Texas.

The V.A.C.® Case Study #7, Case Study, Jun. 1996, 2 pages, 35-D-007, KCI®, San Antonio, Texas.

The V.A.C.® Case Study #6, Case Study, Jun. 1996, 2 pages, 35-D-006, KCI®, San Antonio, Texas.

The V.A.C.® Case Study #9, Case Study, Jun. 1996, 2 pages, 35-D-009, KCI®, San Antonio, Texas.

The V.A.C.® Case Study #5, Case Study, Aug. 1994, 2 pages, 35-D-005, KCI®, San Antonio, Texas.

The V.A.C.® Case Study #4, Case Study, Aug. 1994, 2 pages, 35-D-004, KCI®, San Antonio, Texas.

The V.A.C.® Case Study #3, Case Study, Aug. 1994, 2 pages, 35-D-003, KCI®, San Antonio, Texas.

The V.A.C.® Case Study #2, Case Study, Aug. 1994, 2 pages, 35-D-002, KCI®, San Antonio, Texas.

The V.A.C.® Case Study #1, Case Study, Aug. 1994, 2 pages, 35-D-001, KCI®, San Antonio, Texas.

Ex parte Quayle Office Action dated Feb. 7, 2005 for U.S. Appl. No. 10/275,671.

Amendment filed Apr. 8, 2005 for U.S. Appl. No. 10/275,671.

Non-Final Office Action dated Jun. 27, 2005 for U.S. Appl. No. 10/275,671.

Response filed Oct. 19, 2005 for U.S. Appl. No. 10/275,671.

Non-Final Office Action dated Jan. 10, 2006 for U.S. Appl. No. 10/275,671.

Response filed Jul. 10, 2006 for U.S. Appl. No. 10/275,671.

Supplemental Amendment filed Aug. 10, 2006 for U.S. Appl. No. 10/275,671.

Final Office Action dated Apr. 17, 2007 for U.S. Appl. No. 10/275,671.

Response filed Jun. 12, 2007 for U.S. Appl. No. 10/275,671.

Advisory Action dated Jul. 11, 2007 for U.S. Appl. No. 10/275,671.

Response filed Aug. 17, 2007 for U.S. Appl. No. 10/275,671.

Non-Final Office Action dated Sep. 5, 2007 for U.S. Appl. No. 10/275,671.

Response filed Sep. 5, 2007 for U.S. Appl. No. 10/275,671.

Notice of Allowance and Fee(s) Due dated Feb. 4, 2008 for U.S. Appl. No. 10/275,671.

Restriction Requirement date mailed Nov. 10, 2009 for U.S. Appl. No. 12/127,668.

Response filed Dec. 10, 2009 for U.S. Appl. No. 12/127,668.

Office Action date mailed Mar. 23, 2010 for U.S. Appl. No. 12/127,668.

Response filed Jun. 23, 2010 for U.S. Appl. No. 12/127,668.

Interview Summary date mailed May 25, 2010 for U.S. Appl. No. 12/466,973.

Final Office Action date mailed Aug. 12, 2010 for U.S. Appl. No. 12/466,973.

Non-Final Office Action and Interview Summary date mailed Sep. 6, 2011 for U.S. Appl. No. 12/467,064.

Restriction Requirement date mailed Aug. 12, 2011 for U.S. Appl. No. 12/467,211.

Restriction Requirement date mailed Jul. 21, 2011 for U.S. Appl. No. 12/467,123.

Response filed for U.S. Appl. No. 12/467,123.

Restriction Requirement date mailed Aug. 4, 2011 for U.S. Appl. No. 12/467,153.

Response filed for U.S. Appl. No. 12/467,153.

Final Office Action date mailed Sep. 16, 2010 for U.S. Appl. No. 12/127,668.

Meyer et al, "A new abdominal drain for overflowing lavage in instances of severe pancreatitis with persistent peritoneal contamination", Surg. Gynecol Obstet. Sep. 1987: 165(3): 271-3.

Poritz, "Percutaneous drainage and ileocolectomy for spontaneous intraabdominal abscess in Chrohns Disease" J. Gastrointest Surg. Feb. 2007; 11(2): 204-8.

Khurrum et al, "Percutaneous postoperative intra-abdominal abscess drainage after elective colorectal surgery" Tech Coloprotocl Dec. 2002: 6(3): 159-64.

Reckard et al, "Management of Intraabdominal Hypertension by Percutaneous Catheter Drainage" Journal of Vascular Interventional Journal of Vascular Interventional Radiology, vol. 16, Issue 7, pp. 1019-1021.

Latenser et al, "A Pilot Study Comparing Percutaneous Decompression with decompressive laparotomy for acute abdominal compartment syndrome in thermal injury", J Burn Care & Rehav, 23(3): 190-195.

Kubiak et al, "Reduced intra-peritoneal inflammation by negative pressure therapy moderates systemic inflammation in a porcine modiel of the abdominal compartment Syndrome (ACS) ", Critical Care I, vol. 207, No. 3S, Sep. 2008, S34-35.

Kaplan, "Managing the open abdomen" Ostomy Wound Management, Jan. 2004; 50 1A supply; C2; 1-8.

Kaplan et al, "Guidelines for the Management of the Open Abdomen" WOUNDS Oct. 2005; 17 (Suppl 1); S1S24.

Garner et al, "Vacuum-assisted wound closure provides early fascial reapproximation in trauma patients with open abdomens" The American Journal of Surgery, Dec. 2001; 182 (6); 630-8.

Barker et al, "Vacuum pack of technique of temporary abdominal closure; a 7-year experience with 112 patients" J Trauma Feb. 1, 2000; 48 (2): 201-6.

Brock et a;, "Temporary closure of open abdominal wounds: the vacuum pack" Am Surg Jan. 1995; 61(1): 30-5.

Sherck et al, "Covering the 'open abdomen': a better technique", Am Surg Sep. 1998; 64(9): 854-7.

Dubick et al, "Issues of concern regarding the use of hypertonic/hyperoncotic fluid resuscitation of hemorrhagic hypotension" Shock, Apr. 2006; 25(4): 321-8.

Burdette, "Systemic Inflammatory Response Syndrome", http://emedicine.medscape.com/article/168943-print, Apr. 2007.

Beamis Hyrdorphobic Rigid Canisters—http://www.bemishealthcare.com/docs/CanisterHydrophobic.pdf (date unknown).

Fink et al, "Textbook of Critical Care", 5$^{th}$ ed. (Philadelphia: Elsevier, 2005), 1933-1943.

Smith & Nephew GmbH Nullity Action date mailed Sep. 10, 2010.

Response filed Oct. 4, 2010 for U.S. Appl. No. 12/466,973.

Advisory Action date mailed Oct. 12, 2010 for U.S. Appl. No. 12/466,973.

RCE/Response filed Nov. 2, 2010 for U.S. Appl. No. 12/466,973.

International Search Report and Written Opinion date mailed Oct. 6, 2009; PCT International Application No. PCT/US2009/044266.

International Search Report and Written Opinion date mailed Nov. 5, 2009; PCT International Application No. PCT/US2009/044264.

International Search Report and Written Opinion date mailed Nov. 18, 2009; PCT International Application No. PCT/US2009/044230.

International Search Report and Written Opinion date mailed Sep. 17, 2009; PCT International Application No. PCT/US2009/044240.

International Search Report and Written Opinion date mailed Nov. 5, 2009; PCT International Application No. PCT/US2009/044268.

International Search Report and Written Opinion date mailed Oct. 6, 2009; PCT International Application No. PCT/US2009/044226.

International Search Report and Written Opinion date mailed Oct. 15, 2009; PCT International Application No. PCT/US2009/044244.

International Search Report and Written Opinion date mailed Nov. 5, 2009; PCT International Application No. PCT/US2009/044245.

International Search Report and Written Opinion date mailed Oct. 23, 2009; PCT International Application No. PCT/US2009/044235.

US 6,216,701, 04/2001, Heaton (withdrawn)

MODULAR, REDUCED-PRESSURE, WOUND-CLOSURE SYSTEMS AND METHODS

RELATED APPLICATIONS

The present invention claims the benefit, under 35 USC §119(e), of the filing of U.S. Provisional Patent Application Ser. No. 61/109,410, entitled "Reduced-Pressure, Wound-Closure System and Method," filed Oct. 29, 2008; U.S. Provisional Patent Application Ser. No. 61/109,486, entitled "Reduced-Pressure, Abdominal Treatment System and Method," filed Oct. 29, 2008; U.S. Provisional Patent Application Ser. No. 61/109,390, entitled "Open-Cavity, Reduced-Pressure Wound Dressing and System," filed Oct. 29, 2008; and U.S. Provisional Patent Application Ser. No. 61/109,448, entitled "Reduced-Pressure, Deep-Tissue Closure System and Method," filed Oct. 29, 2008. All of these provisional applications are incorporated herein by reference for all purposes.

BACKGROUND

The present invention relates generally to medical treatment systems and, more particularly, to reduced-pressure, wound-closure and treatment systems and methods.

Whether the etiology of a wound, or damaged area of tissue, is trauma, surgery, or another cause, proper care of the wound is important to the outcome. Unique challenges exist when the wound involves locations that require reentry, such as the peritoneal cavity and more generally the abdominal cavity. Many times when surgery or trauma involves the abdominal cavity, establishing a wound management system that facilitates reentry allows for better and easier care and helps to address such things as peritonitis, abdominal compartment syndrome (ACS), and infections that might inhibit final healing of the wound and the internal organs. In providing such care, it may be desirable to remove unwanted fluids from the cavity, help approximate the fascia and other tissues, or finally to help provide a closing force on the wound itself at the level of the epidermis. Unless otherwise indicated, as used herein, "or" does not require mutual exclusivity.

Currently, an abdominal opening on the epidermis may be closed using sutures, staples, clips, and other mechanical devices. Such devices often cause puncture wounds or can cause other wounds. Moreover, if severe edema occurs, tremendous pressure may be placed on the closure device and the pressure may cause harm. For example, if the pressure rises due to edema, the sutures may tear out.

With respect to an overall system for allowing reentry into the abdominal cavity, a number of techniques have been developed. One approach is to place towels into the cavity and then use clips, such as hemostats, to close the skin over the towels. While simple and fast, the results are regarded as suboptimal. Another approach is the so-called "Bogota bag." With this approach, a bag is sutured into place to cover the open abdomen in order to provide a barrier. Still another approach, sometimes called a "vac pack," is to pack towels in the wound and then place a drain into the abdomen and cover the abdomen with a drape. Finally, a reduced pressure approach has been used. Such an approach is shown in U.S. Pat. No. 7,381,859 to Hunt et al. and assigned to KCI Licensing, Inc. of San Antonio, Tex. U.S. Pat. No. 7,381,859 is incorporated herein by reference for all purposes.

SUMMARY

Problems with existing wound closure devices and reduced-pressure treatment systems are addressed by the systems, apparatus, and methods of the illustrative embodiments described herein. According to an illustrative embodiment, a modular, reduced-pressure, wound-closure system includes a sealed contracting member, a plurality of attachment base members, and a plurality of connecting members. The plurality of attachment base members is movably coupled to the plurality of connecting members to form a circumferential wall defining an interior space. The contracting member is operable to be disposed within the interior space.

According to another illustrative embodiment, a method of manufacturing a modular, reduced-pressure, wound-closure and treatment system for generating a closing force on a surface wound on a patient includes the steps of forming a sealed contracting member, forming a plurality of attachment base members, and forming a plurality of connecting members. The plurality of attachment base members and plurality of connecting members are operable to movably couple to form a circumferential wall defining an interior space.

According to another illustrative embodiment, a method of generating a closing force on a surface wound on a patient includes the steps of providing a sealed contracting member and providing plurality of attachment base members. Each attachment base member has a base and a first wall, which has a first end and a second end. The first end of the first wall includes a first movable connection member and the second end includes a second movable connection member. Each attachment base member is for releasably attaching to a portion of a patient's epidermis and for coupling to the sealed contracting member. The method of generating a closing force further includes providing a plurality of connecting members. Each connecting member of the plurality of connecting members includes a second wall with a first end and a second end. The first end of the second wall has a third movable connection member and the second end of the second wall has a fourth movable connection member. Each connecting member is for movably coupling to two of the plurality of attachment base members. The method of generating a closing force further includes providing reduced pressure to the sealed contracting member. The method of providing a closing force further includes movably coupling the plurality of attachment base members and plurality of connecting members to form a circumferential wall defining an interior space. The method of providing a closing force further includes disposing the sealed contracting member within the interior space and supplying reduced pressure to the contracting member whereby a force is developed that pulls the attachment base members inward to create a closing force on the surface wound.

According to another illustrative embodiment, a reduced-pressure, wound-closure and treatment system for providing a closing force to a surface wound on a patient and for delivering reduced pressure to a tissue site includes a wound-closing subsystem and a reduced-pressure treatment subsystem.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
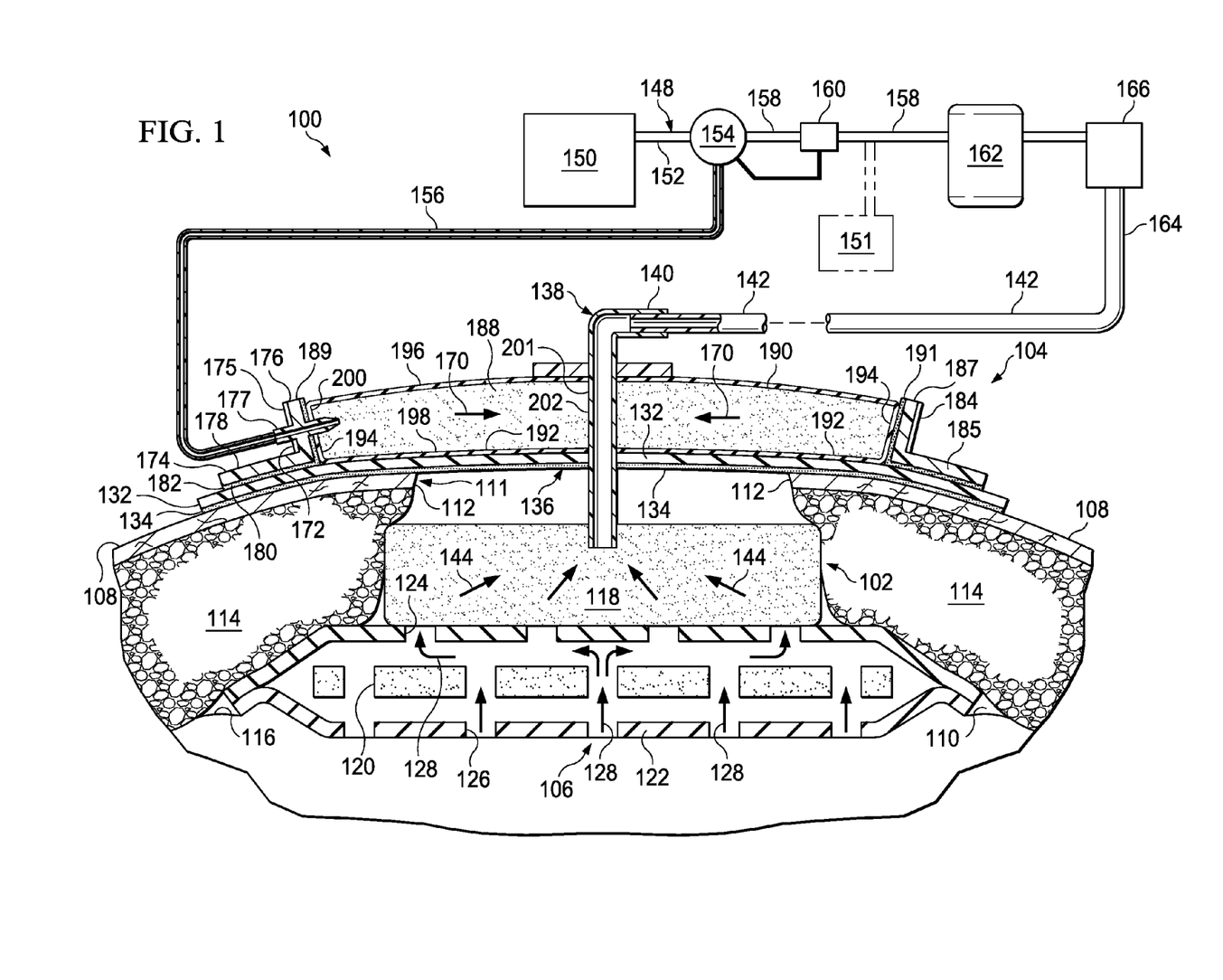
FIG. 1 is a schematic cross-section, with a portion presented as a block diagram, of an illustrative embodiment of a reduced-pressure, wound-closure and treatment system.
Figure 2:
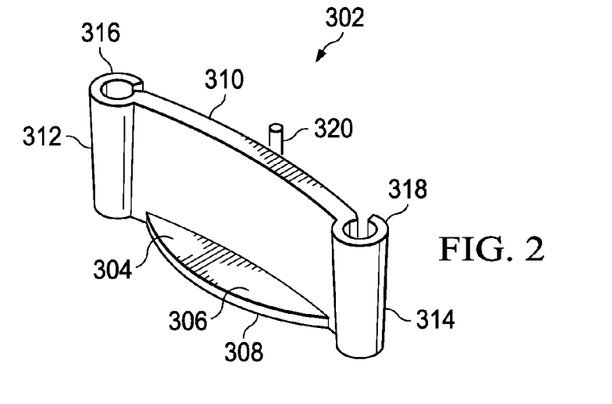
FIG. 2 is a schematic, perspective view of an illustrative embodiment of a attachment base member for use as part of an illustrative embodiment of a reduced-pressure, wound-closure system.

Referring to FIGS. 1-2, and initially to FIG. 1, an illustrative embodiment of a reduced-pressure, wound-closure and treatment system 100 is presented. The reduced-pressure, wound-closure and treatment system 100 may include a reduced-pressure treatment subsystem 102 and a wound-closure subsystem 104. The reduced-pressure treatment subsystem 102 may be used for treating a tissue site 106 with reduced pressure. The tissue site 106 may be the bodily tissue of any human, animal, or other organism, including bone tissue, adipose tissue, muscle tissue, dermal tissue, vascular tissue, connective tissue, cartilage, tendons, ligaments, or any other tissue. The tissue site 106 may be within a body cavity, such as an abdominal cavity 110, and may include various tissue layers including a wound in epidermis 108. Treatment with the reduced-pressure treatment subsystem 102 may include removing fluids, such as ascites or exudates, delivering reduced pressure, or providing a protective barrier.

In the illustrative embodiment, the reduced-pressure, wound-closure and treatment system 100 is presented in the context of the abdominal cavity 110 and a surface wound 111, which has wound edges 112. Other subdermal tissue 114 may also have been opened, such as fat tissue, muscles, fascia, etc. The abdominal cavity 110 is shown with abdominal contents 116, which form a surface or support.

The reduced-pressure treatment subsystem 102 of the reduced-pressure, wound-closure and treatment system 100 helps to deliver reduced pressure to the tissue site 106 and the abdominal cavity 110. The reduced-pressure treatment subsystem 102 includes a manifold 118 disposed within the abdominal cavity 110 to distribute reduced pressure within the abdominal cavity 110 and to receive fluids. The manifold 118 may include or be associated with a manifold member 120, or second manifold, in a non-adherent envelope 122. The non-adherent envelope 122 has apertures 124 on a first side and apertures 126 on a second, inward-facing (tissue-facing) side. The apertures 124 and 126 facilitate flow of fluids as suggested by arrows 128. The apertures 124 and 126 may take any shape, such as rectangular openings, circular openings, polygons, slits (elongated slots), etc. The non-adherent envelope 122 may be formed from a flexible film, such as a polyurethane film, a drape material, or any non-adherent material.

Reduced pressure may be applied by the reduced-pressure treatment subsystem 102 to the abdominal cavity 110 and the tissue site 106 to help promote removal of exudates, ascites, or other liquids, bacteria, fibrin, dead tissue, toxins, residual blood, etc. Reduced pressure may also be used in certain situations to stimulate growth of additional tissue. In the case of a wound at the tissue site 106, the growth of granulation tissue and removal of exudates and bacteria may help to promote healing of the wound. In the situation of a non-wounded or non-defective tissue, reduced pressure may be used to promote the growth of tissue that may be harvested and transplanted to another tissue site. In other situations, fluid removal may be the main reason for applying reduced pressure.

As used herein, "reduced pressure" generally refers to a pressure less than the ambient pressure at the tissue site 106. In most cases, the reduced pressure will be less than atmospheric pressure at which the patient is located. Alternatively, the reduced pressure may be less than the hydrostatic pressure of the tissue site 106. Unless otherwise indicated, values of pressure stated herein are gauge pressures.

The manifold 118 and the manifold member 120 are disposed in the abdominal cavity 110 and may be disposed at or near the tissue site 106. Typically, the non-adherent envelope 122, which contains the manifold member 120, is disposed against the tissue site 106 and, in particular, proximate the abdominal contents 116. The manifold 118 is disposed adjacent the non-adherent envelope 122. The manifold 118 and the manifold member 120 may take many forms. The term "manifold" as used herein generally refers to a substance or structure that is provided to assist in applying reduced pressure to, delivering fluids to, or removing fluids from a tissue site, such as the tissue site 106. The manifold 118 and the manifold member 120 typically include a plurality of flow channels or pathways that are interconnected to improve distribution of fluids provided to and removed from the area proximate the manifold 118 and the manifold member 120. The manifold 118 and the manifold member 120 may be formed from a biocompatible material that is capable of being placed in contact with tissue and that distributes reduced pressure. Examples of manifolds may include, without limitation, devices that have structural elements arranged to form flow channels, cellular foam, such as open-cell foam, porous tissue collections, and liquids, gels and foams that include or cure to include flow channels.

The manifold 118 and manifold member 120 may be porous and may be made from foam, gauze, felted mat, or any other material suited to a particular biological application. In one embodiment, the manifold 118 and manifold member 120 are made from a porous foam that includes a plurality of interconnected cells or pores that act as flow channels. The porous foam may be polyurethane, open-cell, reticulated foam, such as a GranuFoam® material manufactured by Kinetic Concepts, Incorporated of San Antonio, Tex. Other embodiments may include "closed cells" at certain locations to help direct flow. In some situations, the manifold 118, the manifold member 120, and the non-adherent envelope 122 may be used to distribute fluids, such as medications, antibacterials, growth factors, and other solutions to the tissue site 106. Other layers may be included as part of the manifold 118 or manifold member 120, such as absorptive material, wicking material, hydrophobic material, and hydrophilic material.

A sealing member 132 may be placed over the surface wound in the epidermis 108 and, in particular, made to overlap the wound edges 112 to provide a pneumatic seal. Thus, the sealing member 132 provides a seal over the manifold 118 and the non-adherent envelope 122. The sealing member 132 may be a cover that is used to secure the manifold 118 and non-adherent envelope 122 at the tissue site 106. While the sealing member 132 may be impermeable or semi-permeable, the sealing member 132 is capable of maintaining a reduced pressure at the tissue site 106 after installation of the sealing member 132 over the manifold 118. The sealing member 132 may be a flexible over-drape or film formed from a silicone based compound, acrylic, hydrogel or hydrogel-forming material, or any other biocompatible material that includes the impermeability or permeability characteristics desired for the intended tissue site.

The sealing member 132 may further include an attachment device 136 to secure the sealing member 132 to the patient's epidermis 108. The attachment device 136 may take many forms; for example, a sealing tape might be used or an adhesive 134 may be positioned along a perimeter of the sealing member 132 or any portion of the sealing member 132 to provide a pneumatic seal. The adhesive 134 might also be pre-applied and covered with a releasable member (not shown) that is removed at the time of application.

A first reduced-pressure interface 138, or treatment-reduced-pressure interface, such as a port 140, or connector, may be used to deliver reduced pressure from a first reduced-pressure delivery conduit 142 to the manifold 118. The first reduced-pressure interface 138 may also deliver any exudate, ascites, or other fluids from the manifold 118 to the first reduced-pressure delivery conduit 142. The reduced pressure in the manifold 118 pulls the fluid in the direction shown by arrows 144 and to the first reduced-pressure delivery conduit 142. The first reduced-pressure interface 138 permits the passage of fluid from the manifold 118 to the first reduced-pressure delivery conduit 142. For example, fluids collected from the tissue site 106 using the manifold member 120 and the manifold 118 may enter the first reduced-pressure delivery conduit 142 via the first reduced-pressure interface 138. In another embodiment, the reduced-pressure treatment subsystem 102 may exclude the first reduced-pressure interface 138, and the first reduced-pressure delivery conduit 142 may be inserted directly into the sealing member 132 and the manifold 118. The first reduced-pressure delivery conduit 142 may be a medical conduit, multi-lumen member, tubing, or any other means for delivering a reduced pressure.

A reduced-pressure subsystem 148 may be used to supply reduced pressure that is delivered to the first reduced-pressure delivery conduit 142. The reduced-pressure subsystem 148 may include a first reduced-pressure unit, or source, 150 that delivers reduced pressure to a conduit 152, which delivers reduced pressure to a three-way valve 154. One portion of the reduced pressure may leave the three-way valve 154 through the second reduced-pressure delivery conduit 156. Another portion of the reduced pressure may leave the three-way valve 154 through a reduced-pressure conduit 158. Located on the reduced-pressure conduit 158 may be any number of devices, such as a reduced-pressure feedback unit 160, which may, for example, give feedback to the three-way valve 154 concerning the regulation of the reduced pressure within the reduced-pressure conduit 158. The reduced-pressure conduit 158 delivers the reduced pressure to a canister 162, which is operable to hold any fluids delivered to the canister 162 from the tissue site 106. Reduced pressure leaving the canister 162 is delivered to the first reduced-pressure delivery conduit 142. The first reduced-pressure delivery conduit 142 may be referred to as delivering a treatment-reduced-pressure because the reduced pressure therein has been placed, by the reduced-pressure subsystem 148, at the desired pressure and conditions for use in reduced-pressure treatment at the tissue site 106. The reduced pressure delivered to the first reduced-pressure delivery conduit 142 is typically selected to be in the range −50 mm Hg to −500 mm Hg at the tissue site and more typically between −100 mm Hg and −300 mm Hg.

A number of different devices, e.g., representative device 166, may be added to a medial portion 164 of the first reduced-pressure delivery conduit 142. The representative device 166 may be a pressure feedback device, a volume detection system, a blood detection system, an infection detection system, a flow monitoring system, a temperature monitoring system, etc. Some of these devices may be formed integrally to other parts; for example, the canister 162 may include one or more filters, e.g., a hydrophobic filter that prevents liquid from exiting.

There are many ways of developing the reduced pressure to be used with the reduced-pressure, wound-closure and treatment system 100. In the illustrative embodiment shown, the first reduced-pressure unit 150 is used for both applications, i.e., for wound closing and for reduced-pressure treatment. In an alternative embodiment, it may be desirable to use the first reduced-pressure unit 150 as the source for the second reduced-pressure delivery conduit 156 and have a second reduced-pressure unit 151 (shown in broken lines) to deliver reduced pressure to the reduced-pressure conduit 158.

As an aspect of the reduced-pressure, wound-closure and treatment system 100, it is also desirable to help provide a closing force to the surface wound 111 and in particular to apply a closing force between the wound edges 112. As shown in FIG. 1, the wound-closure subsystem 104 may be used for this purpose. The wound-closure subsystem 104 develops a closing force represented by arrows 170. The closing force is communicated to the epidermis 108 and urges the wound edges 112 towards each other. The wound-closure subsystem 104 may be a stand alone system for closing any surface wound or used as part of a larger system, e.g., the reduced-pressure, wound-closure and treatment system 100.

The wound-closure subsystem 104 may include a plurality of attachment base members, e.g., a first attachment base member 172 and a second attachment base member 184. Each of the attachment base members movably couples with a connecting member (analogous to first connecting member 326 in FIG. 3 below) to form a circumferential wall (analogous to circumferential wall 380 in FIG. 5A below) with an interior space (analogous to interior space 381 in FIG. 5A below). A sealed contracting member 188 is disposed within the interior space and coupled to at least two of the attachment base members, e.g., the first attachment base member 172 and the second attachment base member 184. The circumferential wall is operable to flex or move as the sealed contracting member 188 contracts.

The first attachment base member 172 has a first base 174 and a first wall 176. The first base 174 has a first side 178 and a second, inward-facing side 180. The first base 174 and first wall 176 may be made from numerous materials, but a material is preferred that provides flexibility; for example, the first attachment base member 172 may be formed with the first base 174 and the first wall 176 made from polypropylene, or a rigid silicone, etc. A first adhesive 182 may be applied to the second, inward-facing side 180 of the first base 174 to allow the first base 174 to be releasably attached directly to a portion of the patient's epidermis 108 or indirectly if a polyurethane film or other sealing member 132 is placed on the epidermis 108 first. In addition to the first adhesive 182, staples, or sutures, or other invasive approaches might be used in some situations to attach the first base 174 to intact epidermis tissue. The first attachment base member 172 may be applied directly on top of the epidermis 108 or on top of the sealing member 132 so that closing forces applied on the first attachment base member 172 are transmitted directly, or indirectly, to the epidermis 108. References to applying the first attachment base member 172 to the epidermis 108 should be deemed to include application on the sealing member 132 as well. The first attachment base member 174 may include a movable connection member 175, which is sized and configured to mate with another movable connection member (see, e.g., third movable connection member 334 in FIG. 3), and a second reduced-pressure interface 177, or closing-reduced-pressure interface, which facilitates delivery of reduced pressure to the sealed contracting member 188.

The second attachment base member 184 is analogous to the first attachment base member 172, except the second attachment base member 184 does not include the second reduced-pressure interface 177. The second attachment base member 184 has a base 185 and a wall 187. While the wound-closure subsystem 104 only shows two attachment base members 172, 184 other attachment members may be dispersed around the surface wound 111 in a spaced fashion with connecting members between to form the circumferential wall around the surface wound 111. The attachment base members, e.g., attachment base members 172, 184, in conjunction with the sealed contracting member 188 allow the closing force, which is represented by arrows 170, to be developed across different shapes of the surface wounds 111.

One or more of the attachment base members, e.g., attachment base member 172, has the second reduced-pressure interface 177 for receiving reduced pressure from the second reduced-pressure delivery conduit 156. The reduced pressure delivered through the second reduced-pressure interface 177 is used to develop the closing force. The reduced pressure, or closing-reduced-pressure, in the second reduced-pressure delivery conduit 156 may be selected to be in the range −100 mm Hg to −1000 mm Hg.

The wound-closure subsystem 104 includes the sealed contracting member 188 to develop the closing force. The sealed contracting member 188 may be formed from a contracting manifold material, which may be the same type of material as the manifold 118. Alternatively, it may be desirable to use a contracting manifold material that has fewer apertures or holes than the material used for the manifold 118. In addition, it may be desirable to have a material that will contract less in the vertical (for the orientation shown in FIG. 1) and more in the horizontal, or lateral, plane (for the orientation shown in FIG. 1), i.e., an anisotropic material. The sealed contracting member 188 has a first side 190 and a second, inward-facing (tissue-facing) side 192.

The sealed contracting member 188 also has a peripheral edge 194. The sealed contracting member 188 may be sealed by having a first sealing member 196 applied to the first side 190 and a second sealing member 198 applied to the second, inward-facing (tissue-facing) side 192 of the sealed contracting member 188. The peripheral edge 194 of the sealed contracting member 188 may be sealed by a peripheral sealing member 200. Alternatively or in addition, the first wall member 176 may also be used as the peripheral sealing member to seal the peripheral edge 194 or another piece of sealed material may be used. Similarly, the second, inward-facing (tissue-facing) side 192 may be sealed by placement against the sealing member 132 or the patient's epidermis 108. The sealed contracting member 188 may also be sealed by being coated with a gas-impervious material. The sealed contracting member 188 may be sealed with the first and second sealing members 196, 198, which may be formed from a polyurethane film or silicone. The first and second sealing members 196, 198 may be ultrasonically welded or RF welded at their ends to cover the peripheral edge 194. When reduced pressure is supplied to the sealed contracting member 188, the sealed contracting member 188 contracts to develop a closing force, which is represented by arrows 170. The sealed contracting member 188 may be formed with an opening 201 on a portion of the sealed contracting member 188 for receiving an extension portion 202 of the first reduced-pressure interface 138. The extension portion 202 may extend through the sealed contracting member 188 and into the manifold 118.

In operation, the reduced-pressure wound-closure and treatment system 100 may be used in a body cavity, e.g., the abdominal cavity 110, by first applying a manifold material on the abdominal contents 116. For example, the manifold member 120 with the non-adherent envelope 122 may be placed on the abdominal contents 116 and the manifold 118 disposed proximate the non-adherent envelope 122. The wound edges 112 of the surface wound 111 may be brought together to the extent possible, and then the sealing member 132 placed onto the epidermis 108 to provide a pneumatic seal over the surface wound 111. The first attachment base member 172 may be applied using the first adhesive 182 to the patient's epidermis 108 or on the sealing member 132. Then, connection members and attachment members may be disposed around the surface wound 111. The attachment members, e.g., first and second attachment base members 172, 184, are coupled to the patient's epidermis 108 (or sealing member) and the sealed contracting member 188 is coupled to the attachment members, e.g., first and second attachment base members 172, 184. This coupling between attachment members, e.g., first and second attachment base members 172, 184, and the sealed contracting member 188 may be accomplished in a number of different ways, such as by using adhesives 189 and 191.

The first reduced-pressure interface 138, which may be the reduced-pressure port 140, may be applied such that the extended portion 202 reaches into the manifold 118. The first reduced-pressure delivery conduit 142 may be coupled to the first reduced-pressure interface 138 to provide a fluid coupling with the first reduced-pressure unit 150 (or an optional second reduced-pressure unit 151). The second reduced-pressure delivery conduit 156 may be fluidly coupled to the second reduced-pressure interface 177.

The reduced-pressure, wound-closure treatment system 100 is activated such that the first reduced-pressure unit 150 delivers reduced pressure through the three-way valve 154, which prepares the treatment-reduced-pressure that is delivered to the first reduced-pressure delivery conduit 142 and a closing-reduced-pressure that is delivered to the second reduced-pressure delivery conduit 156. The treatment-reduced-pressure is delivered through the first reduced-pressure delivery conduit 142 and realized at the manifold 118, which pulls fluids as suggested by arrows 144 and 128 and distributes reduced pressure within the abdominal cavity 110. At the same time, the closing-reduced-pressure delivered through the second reduced-pressure delivery conduit 156 is realized by the sealed contracting member 188, which causes the sealed contracting member 188 to contract developing the closing force, which is represented by arrows 170. The closing force pulls the first and second attachment base members 172, 184 towards each other and thereby pulls the wound edges 112. The reduced-pressure, wound-closure treatment system 100 may be used solely to close a wound in some applications.

Referring now to FIGS. 2 to 5B, a portion of a modular, reduced-pressure, wound-closure system 300 will now be presented. The modular, reduced-pressure, wound-closure system 300 uses a number of modular components that may be movably coupled to accommodate various sizes and shapes of wounds and to provide a closing force directed toward a center of the wound, i.e., one that urges the wound edges together. The use of modular components allows numerous sizes and shapes of surface wounds to be accommodated without requiring a large stock of different sizes and shapes of wound dressings or devices.

Referring primarily to FIG. 2, a plurality of attachment base members, such as a first attachment base member 302, may be used. Each attachment base member 302 has a base 304, which has a first side 306 and a second, inward-facing (tissue-facing) side 308. The second, inward-facing (tissue-facing) side 308 of the base 304 may have an adhesive (not explicitly shown) for attaching the first attachment base member 302 to a patient's epidermis (or to a sealing member on the patient's epidermis). In an alternative embodiment, mechanical devices, e.g., sutures, may also be used to secure the first attachment base member 302 to the patient's epidermis. The adhesive on the second, inward-facing side 308 may initially be covered with a releasable backing material that may be removed before application to the patient's epidermis. The first attachment base member 302 also includes a wall 310 that is coupled to the base 304, e.g., attached or formed integral with the base 304. The wall 310 has a first end 312 and a second end 314. The first end 312 may be formed with a first movable connection member 316 formed as an integral part or attached to the wall 310. The second end 314 may be formed with a second movable connection member 318 formed as an integral part or attached to the wall 310. A hook member 320, as described further below, may be used to pierce, grip, or hold a sealed contracting member 322. The hook member 320 may be formed integral to or attached to the wall 310 or the base 304.

Figure 3:
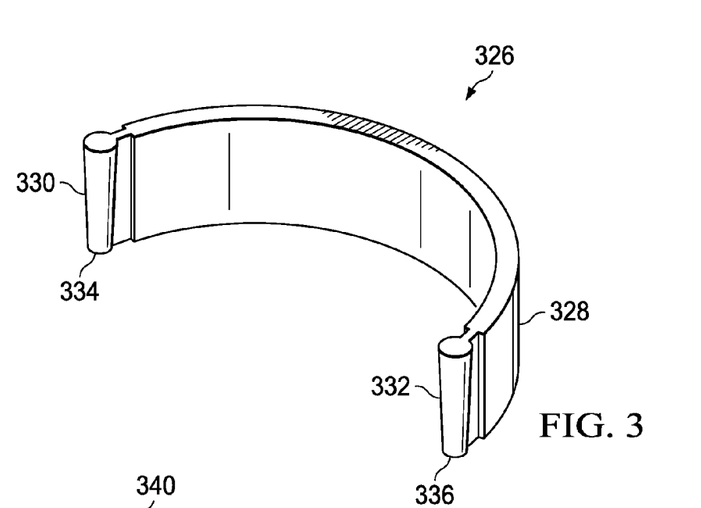
FIG. 3 is a schematic, perspective view of an illustrative embodiment of a connection member for use as part of an illustrative embodiment of a reduced-pressure, wound-closure system.

Referring now primarily to FIG. 3, a plurality of connecting members, such as the first connecting member 326, may be used as part of the modular, reduced-pressure, wound-closure system 300. Each connecting member 326 has a second wall 328 with a first end 330 and second end 332. The second wall 328 may be shaped to have an arcuate configuration or may be straight. The first end 330 may be formed with, or have coupled to the first end 330, a third movable connection member 334. Similarly, the second end 332 may be formed with, or have coupled to the second end 332, a fourth movable connection member 336. The movable connection members 334 and 336 are sized and configured to cooperate with the movable connection members 316 and 318 in a coordinated fashion that allows relative movement, such as pivotable movement, between each attachment base member 302 and each adjacent, coupled connecting member 326. In this illustrative embodiment, the movable connection members 334 and 336 are shown as being pin-shaped members that are sized and configured to slide into the first and second movable connection members 316 and 318, which are sockets, sized and configured to receive the pin shapes of the movable connection members 334 and 336. Of course, the pin-shaped members and sockets could be arranged vice-versa or mixed and matched.

Figure 4:
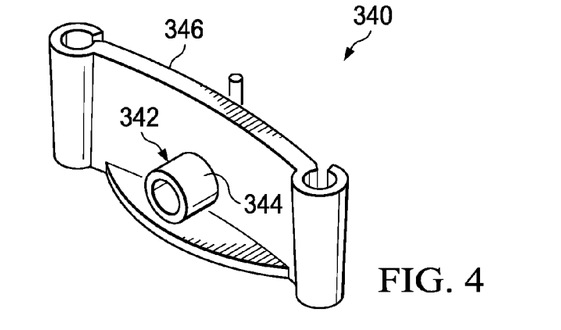
FIG. 4 is a schematic, perspective view of an illustrative embodiment of a reduced-pressure interface member for use as part of an illustrative embodiment of a reduced-pressure, wound-closure system.

While a reduced-pressure conduit, such as the second reduced-pressure delivery conduit 156 in FIG. 1, may be applied directly through the wall 310, a reduced-pressure interface 342 may be used on the wall 310 of the first attachment base member 302. For example, the first attachment base member 302 may be modified to form a reduced-pressure interface member 340 as shown in FIG. 4. The reduced-pressure interface member 340 is analogous to that of the first attachment base member 302 except that the reduced-pressure interface 342 has been added. The reduced-pressure interface 342 may be a port 344 that extends through a wall 346. Alternatively, a reduced-pressure interface may be formed with a port, e.g., port 344, placed through the connecting member 326.

Figure 5A:
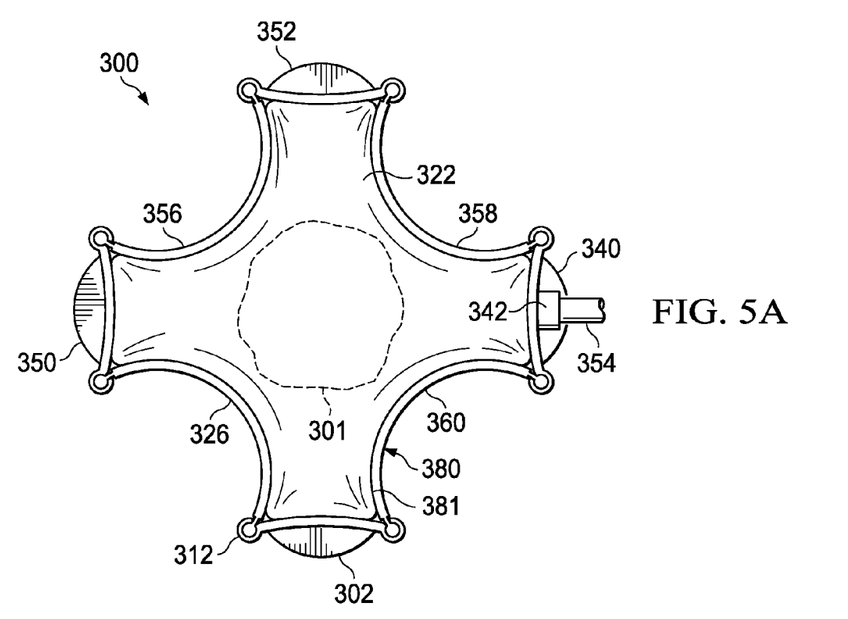
FIGS. 5A and 5B are schematic, plan views of an illustrative embodiment of a reduced-pressure, wound-closure system in a non-contracted position (FIG. 5A) and a contracted position (FIG. 5B)
Figure 5B:
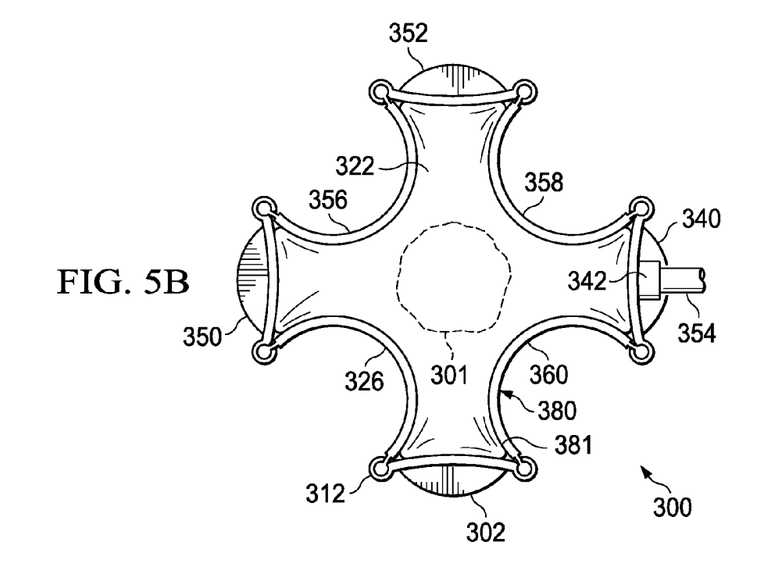

The previously presented modular components, i.e., the first attachment base member 302, the first connecting member 326, and the reduced-pressure interface member 340, may be combined to form various shapes and thereby to accommodate wounds of different sizes and shapes. One example is shown in FIGS. 5A and 5B. The combined members form the modular, reduced-pressure, wound-closure system 300 over a surface wound 301. With reference particularly to FIG. 5A, the modular, reduced-pressure, wound-closure system 300 is shown with a plurality of attachment base members: the first attachment base member 302, a second attachment base member 350, and a third attachment base member 352. A fourth attachment base member is shown but has been modified to form the reduced-pressure interface member 340 having the reduced-pressure interface 342. A reduced-pressure conduit 354 may be fluidly coupled to the reduced-pressure interface 342.

A plurality of connecting members is used to connect each of the plurality of attachment base members 302, 350, 352, 340 (interface). Thus, in this illustrative embodiment, the first attachment base member 302 is coupled at the first end 312 to the first connecting member 326 at the second end 332 of the first connecting member 326. Similarly, the second attachment base member 350 is coupled to a second connecting member 356. The second connecting member 356 is also coupled to the third attachment base member 352. The third attachment base member 352 is coupled to a third connecting member 358, which is also coupled to the reduced-pressure interface member 340. The reduced-pressure interface member 340 is coupled to a fourth connecting member 360. In this way the plurality of attachment base members and plurality of connecting members form a circumferential wall 380 defining an interior space 381 into which a sealed contracting member 322 is disposed. The sealed contracting member 383 may be held proximate the attachment base members by hooks, e.g., hook 320 on the first attachment base member 302, or by adhesive, bonding, welding, or other attachment device. The sealed contracting member 322 may be attached to all or a portion of the circumferential wall 380.

Figure 6:
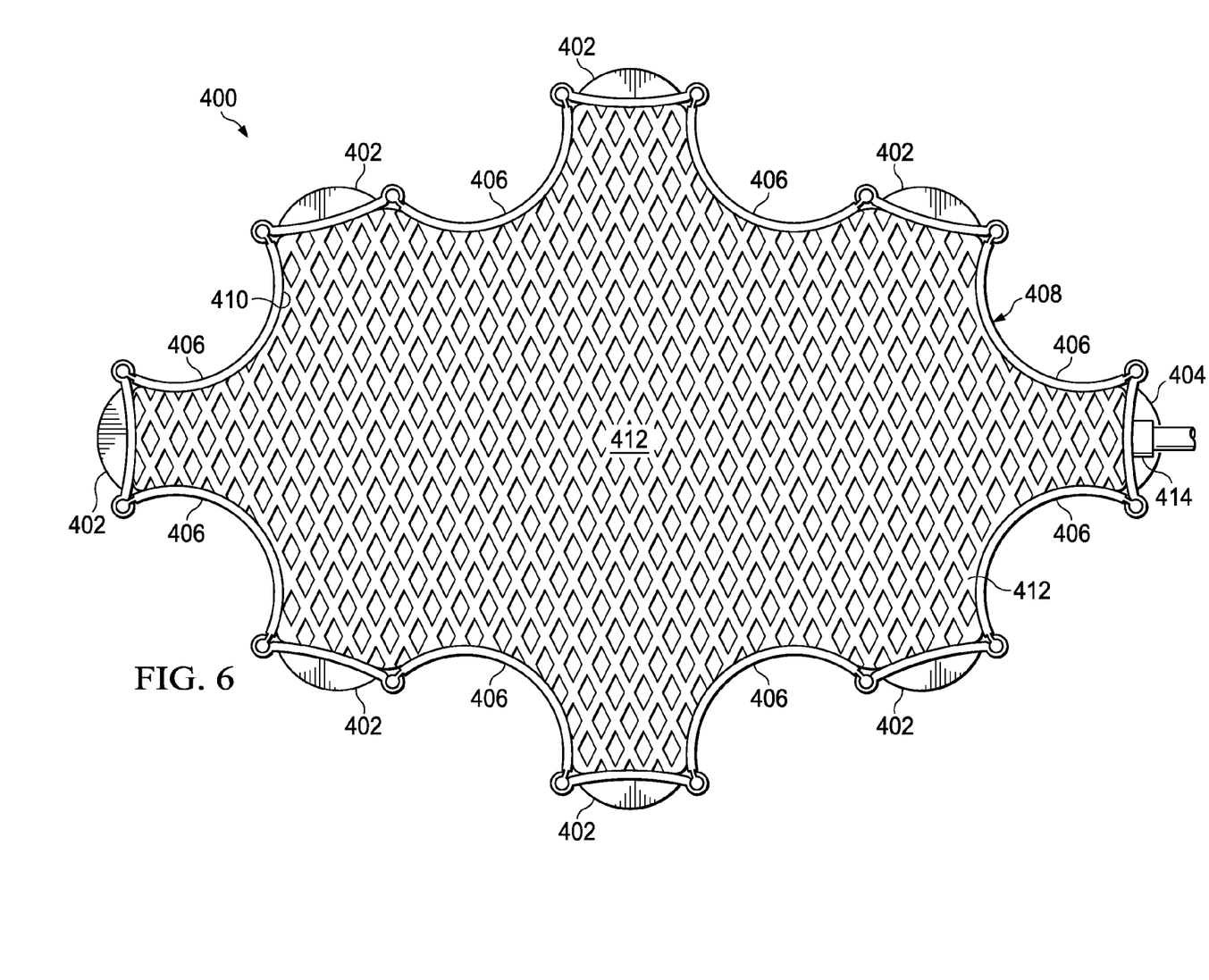
FIG. 6 is schematic, perspective view of an illustrative embodiment of a reduced-pressure, wound-closure system.

It will be appreciated that the alternating members of the plurality of attachment base members and plurality of connecting members provide for connections that are capable of movement. This movement is helpful when the modular, reduced-pressure, wound-closure system 300 goes from the non-contracted position of FIG. 5A to the contracted position shown in FIG. 5B. It will also be appreciated that while only four connecting members and four attachment base members are shown in this illustration, any number of these components might be used to make bigger or smaller systems. For example, a modular, reduced-pressure wound-closure system 400 in FIG. 6 shows a larger system configuration.

The modular, reduced-pressure, wound-closure system 400 in this illustrative embodiment includes a plurality of attachment base members having seven attachment base members 402 and another that has been modified to form a reduced-pressure interface 404. The modular, reduced-pressure, wound-closure system 400 also includes a plurality of connecting members, which in this illustrative embodiment includes eight connecting members 406. The plurality of attachment base members 402 and the plurality of connecting members 406 are movably coupled to form a circumferential wall 408 that defines an interior space 410. A sealed contracting member 412 is placed within the interior space 410 and is coupled to at least the plurality of attachment base members 402. The sealed contracting member 412 may be coupled using hooks on the plurality of attachment base members 402 in a manner analogous to the hook 320 of FIG. 2 or other attachment device. When reduced pressure is supplied through a reduced-pressure interface 414 on the reduced-pressure interface member 404, the reduced pressure causes the sealed contracting member 412 to contract and pulls each of the plurality of attachment base members 402 inward and thus provides a closing force.

Although the present invention and its advantages have been disclosed in the context of certain illustrative, non-limiting embodiments, it should be understood that various changes, substitutions, permutations, and alterations can be made without departing from the scope of the invention as defined by the appended claims.

We claim:

1. A modular, reduced-pressure, wound-closure system for generating a closing force on a surface wound on a patient, the system comprising:
    a sealed contracting member, the sealed contracting member operable to contract when placed under reduced pressure;
    a plurality of attachment base members, each attachment base member having a base and a first wall, the first wall having a first end and a second end, the first end of the first wall having a first movable connection member and the second end of the first wall having a second movable connection member, each attachment base member for releasably attaching to a portion of a patient's epidermis and for coupling to the sealed contracting member;
    a plurality of connecting members, each connecting member having a second wall with a first end and a second end, the first end of the second wall having a third movable connection member and the second end of the second wall having a fourth movable connection member, each connecting member for movably coupling to one of the plurality of attachment base members;
    a first reduced-pressure interface fluidly coupled to the sealed contracting member, the first reduced-pressure interface operable to deliver reduced pressure to the sealed contracting member; and
    wherein the plurality of attachment base members and the plurality of connecting members are operable to movably couple to form a circumferential wall defining an interior space and wherein the sealed contracting member is operable to be disposed and coupled within the interior space.

2. The modular, reduced-pressure, wound-closure system of claim 1, wherein the first movable connection member and the second movable connection member of each of the plurality of attachment base members comprise pin-shaped members and wherein the third movable connection member and the fourth movable connection member of each of the plurality of connecting members comprises sockets sized and configured to mate with the pin shaped members of the plurality of attachment base members.

3. The modular, reduced-pressure, wound-closure system of claim 1 wherein the plurality of attachment base members are coupled to the sealed contracting member by a first adhesive and the plurality of connecting members are coupled to the sealed contracting member by a second adhesive.

4. The modular, reduced-pressure, wound-closure system of claim 1, wherein the reduced-pressure interface comprises a port formed on the circumferential wall.

5. The modular, reduced-pressure, wound-closure system of claim 1 wherein the plurality of attachment base members and the plurality of connecting members comprise a flexible material.

6. The modular, reduced-pressure, wound-closure system of claim 1 further comprising a hook member coupled to a portion of at least one of the plurality of attachment base members and wherein the hook member is operable to secure at least a portion of the sealed contracting member.

7. The modular, reduced-pressure, wound-closure system of claim 1, further comprising a hook member coupled to a portion of at least one of the plurality of attachment base members and wherein the hook member is operable to secure at least a portion of the sealed contracting member; and wherein:
    the first movable connection member and the second movable connection member of each of the plurality of attachment base members comprises a pin-shaped member;
    the third movable connection member and the fourth movable connection member of each of the plurality of connecting members comprises sockets sized and configured to mate with the pin-shaped members of the plurality of attachment base members; and
    the plurality of attachment base members and the plurality of connecting members comprise a flexible material.

8. A method of manufacturing a modular, reduced-pressure, wound-closure system for generating a closing force on a surface wound on a patient, the method comprising the steps of:
    forming a sealed contracting member, the sealed contracting member operable to contract when subjected to reduced pressure;
    forming a plurality of attachment base members, each attachment base member having a base and a first wall, the first wall having a first end and a second end, the first end of the first wall having a first movable connection member and the second end of the first wall having a second movable connection member, each attachment base member for releasably attaching to a portion of a patient's epidermis and for coupling to the sealed contracting member;
    forming a plurality of connecting members, each connecting member having a second wall with a first end and a second end, the first end of the second wall having a third movable connection member and the second end of the second wall having a fourth movable member, each connecting member for movably coupling to at least two of the plurality of attachment base members; and
    wherein the plurality of attachment base members and the plurality of connecting members are operable to movably couple to form a circumferential wall defining an interior space.

9. The method of manufacturing a modular, reduced-pressure, wound-closure system of claim 8, wherein the step of forming a plurality of attachment base members comprises forming each of the plurality of attachment base members with the first movable connection member and the second movable connection member formed as pin-shaped members; and wherein the step of forming a plurality of connecting members comprises forming each of the plurality of connecting members with the third movable connection member and the fourth movable connection member formed as sockets sized and configured to mate with the pin-shaped members of the plurality of attachment base members.

10. The method of manufacturing a modular, reduced-pressure, wound-closure system of claim 8, further comprising the steps of coupling the plurality of attachment base members to the sealed contracting member and coupling the plurality of connecting members to the sealed contracting member.

11. The method of manufacturing a modular, reduced-pressure, wound-closure system of claim 8, further comprising the step of coupling a hook member to a portion of at least one of the plurality of attachment base members.

12. The method of manufacturing a modular, reduced-pressure, wound-closure system of claim 8, further comprising the steps of:
   coupling a hook member to a portion of at least one of the plurality of attachment base members;
   wherein the step of forming a plurality of attachment base members comprises forming each of the plurality of attachment base members with the first movable connection member and the second movable connection member formed as pin-shaped members; and
   wherein the step of forming a plurality of connecting members comprises forming each of the plurality of connecting members with the third movable connection member and the fourth movable connection member formed as sockets sized and configured to mate with the pin-shaped members of the plurality of attachment base members.

13. A method for generating a closing force on a surface wound on a patient, the method comprising the steps of:
   providing a sealed contracting member;
   providing a plurality of attachment base members, each attachment base member having a base and a first wall, the first wall having a first end and a second end, the first end of the first wall having a first movable connection member and the second end having a second movable connection member, each attachment base member for releasably attaching to a portion of a patient's epidermis;
   providing a plurality of connecting members, each connecting member having a second wall with a first end and a second end, the first end of the second wall having a third movable connection member and the second end of the second wall having a fourth movable connection member, each connecting member for movably coupling to the plurality of attachment base members;
   movably coupling the plurality of attachment base members and plurality of connecting members to form a circumferential wall defining an interior space;
   disposing the sealed contracting member within the interior space;
   coupling the sealed contracting member to at least a portion of the circumferential wall; and
   supplying reduced pressure to the sealed contracting member, whereby a force is developed that pulls the attachment base members towards an interior of the surface wound to create a closing force on the surface wound.

14. The method for generating a closing force on a surface wound on a patient of claim 13, wherein the step of providing a plurality of attachment base members comprises providing a plurality of attachment base members wherein the first movable connection member and the second movable connection member of each of the plurality of attachment base members comprises pin-shaped members; and wherein the step of providing a plurality of connecting members comprises providing a plurality of connecting members wherein the third movable connection member and the fourth movable connection member of each of the plurality of connecting members comprises sockets sized that are sized and configured to mate with the pin-shaped members of the plurality of attachment base members.

15. The method for generating a closing force on a surface wound on a patient of claim 13, wherein the step of coupling the sealed contracting member to at least a portion of the circumferential wall comprises coupling the plurality of attachment base members to the sealed contracting member.

16. The method for generating a closing force on a surface wound on a patient of claim 13, further comprising the step of forming a reduced-pressure interface on a portion of the circumferential wall and wherein the step of supplying reduced pressure to the sealed contracting member comprises supplying reduced pressure to the reduced-pressure interface.

17. A reduced-pressure, wound-closure and treatment system for providing a closing force to a surface wound on a patient and for delivering reduced pressure to a tissue site, the system comprising:
   a wound-closing subsystem comprising:
      a sealed contracting member, the sealed contracting member operable to contract when placed under reduced pressure,
      a plurality of attachment base members, each attachment base member having a base and a first wall, the first wall having a first end and a second end, the first end of the first wall having a first movable connection member and the second end of the first wall having a second movable connection member, each attachment base member for releasably attaching to a portion of a patient's epidermis and for coupling to the sealed contracting member,
      a plurality of connecting members, each connecting member having a second wall with a first end and a second end, the first end of the second wall having a third movable connection member and the second end of the second wall having a fourth movable connection member, each connecting member for movably coupling to the plurality of attachment base members,
      a closing-reduced-pressure interface fluidly coupled to the sealed contracting member, the first reduced-pressure interface operable to deliver reduced pressure to the sealed contracting member,
      wherein the plurality of attachment base members and the plurality of connecting members are operable to movably couple to form a circumferential wall defining an interior space and wherein the sealed contracting member is operable to be disposed and coupled within the interior space, and
   a reduced-pressure treatment subsystem comprising:
      a manifold for disposing proximate the tissue site, the manifold operable to distribute reduced pressure and to receive fluids,
      a sealing member for placement on the patient's epidermis and operable to form a pneumatic seal over the manifold, and
      a treatment-reduced-pressure interface for fluidly coupling to the manifold, the treatment-reduced-pressure interface operable to deliver a second reduced pressure to the manifold.

18. The reduced-pressure, wound-closure and treatment system for providing a closing force to a surface wound on a patient and for delivering reduced pressure to a tissue site of claim 17, wherein the first movable connection member and the second movable connection member of each of the plurality of attachment base members comprises pin-shaped members and wherein the third movable connection member and the fourth movable connection member of each of the plurality of connecting members comprises sockets sized and configured to mate with the pin-shaped members of the plurality of attachment base members.

19. The reduced-pressure, wound-closure and treatment system for providing a closing force to a surface wound on a patient and for delivering reduced pressure to a tissue site of claim 17, wherein the plurality of attachment base members are coupled to the sealed contracting member by an adhesive.

20. The reduced-pressure, wound-closure and treatment system for providing a closing force to a surface wound on a patient and for delivering reduced pressure to a tissue site of claim 17, wherein the plurality of attachment base members and the plurality of connecting members comprise a flexible material.

21. The reduced-pressure, wound-closure and treatment system for providing a closing force to a surface wound on a patient and for delivering reduced pressure to a tissue site of claim 17, further comprising a hook member coupled to a portion of at least one of the plurality of attachment base members and wherein the hook member is operable to secure at least a portion of the sealed contracting member.

22. The reduced-pressure, wound-closure and treatment system for providing a closing force to a surface wound on a patient and for delivering reduced pressure to a tissue site of claim 17, further comprising a hook member coupled to a portion of at least one of the plurality of attachment base members and wherein the hook member is operable to secure at least a portion of the sealed contracting member; and wherein:
 the first movable connection member and the second movable connection member of each of the plurality of attachment base members comprises pin-shaped members;
 the third movable connection member and the fourth movable connection member of each of the plurality of connecting members comprises sockets sized and configured to mate with the pin-shaped members of the plurality of attachment base members; and
 the plurality of attachment base members and the plurality of connecting members comprise a flexible material.

\* \* \* \* \*